United States Patent [19]

McGowan et al.

[11] Patent Number: 4,560,873

[45] Date of Patent: Dec. 24, 1985

[54] SITU MULTI-CHANNEL COMBUSTION GAS ANALYZER

[75] Inventors: Gerald F. McGowan, Parker; Gerald W. Price, Morrison; Carl E. Polhemus, Englewood; Ronald L. Ketchum, Littleton, all of Colo.

[73] Assignee: Lear Siegler, Inc., Englewood, Colo.

[21] Appl. No.: 505,201

[22] Filed: Jun. 17, 1983

[51] Int. Cl.⁴ .............................................. G01N 21/35
[52] U.S. Cl. ..................................... 250/339; 250/343; 250/351; 356/439
[58] Field of Search ............... 250/339, 343, 341, 351; 356/438, 439

[56] References Cited

U.S. PATENT DOCUMENTS

| 3,796,887 | 3/1974 | Vincent et al. | 356/439 |
| 4,013,260 | 3/1977 | McClatchie et al. | 250/343 |
| 4,153,837 | 5/1979 | Ross | 250/343 |
| 4,323,777 | 4/1982 | Baskins et al. | 250/339 |
| 4,480,191 | 10/1984 | Karpowycz | 250/343 |

OTHER PUBLICATIONS

W. B. Telfair, A. C. Gilby, R. J. Syrjala and P. A. Wilks, Jr., "A Microcomputer-Controlled Infrared Analyzer for Multi-Component Analysis", *American Laboratory*, vol. 8, No. 11 (Nov. 1976) pp. 91–100.

*Primary Examiner*—Alfred E. Smith
*Assistant Examiner*—Constantine Hannaher
*Attorney, Agent, or Firm*—Fields, Lewis, Pittenger & Rost

[57] ABSTRACT

Apparatus is disclosed to accurately measure and analyze multiple component interfering gases which coexist in the stack gas effluent generated from a combustion process which utilizes a non-dispersive, narrowband infrared absorption technique. The apparatus includes a probe in the stack with an optical measurement cavity (34) through which the stack gases are passed. A transceiver (14) mounted to the probe includes an optical portion operatively associated with the measurement cavity including a chopped light source (54), (60), (62) for projecting beams of light into the measurement cavity and a detector (86) for detecting the attenuation of the gases to provide a measure of the extent of absorption of each gas of interest. A control unit, preferably remote from the transceiver, preferably a programmed digital computer, and preferably via a J-box (18) converts the electric outputs to a corresponding % modulation and in turn corrects for temperature, pressure and interference between gases. The results may be displayed on a front panel (174) or used, for example, to maximize efficiency in a combustion process.

16 Claims, 16 Drawing Figures

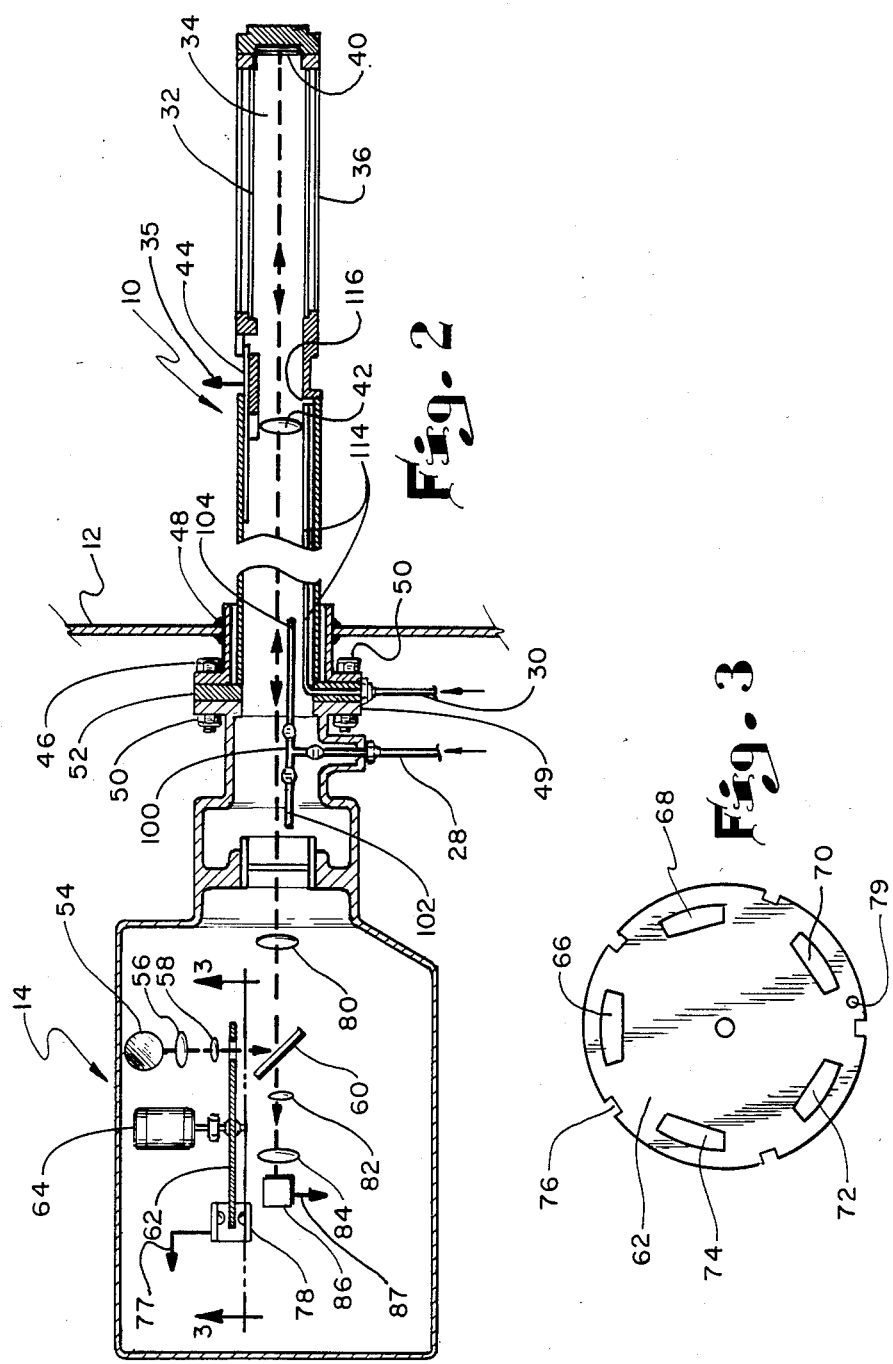

SITU MULTI-CHANNEL COMBUSTION GAS ANALYZER

DESCRIPTION

1. Technical Field

This invention relates to a combustion gas analyzer for a smoke stack and more particularly for one which will accurately measure the concentration of any one of several gases in the smoke stack with high accuracy, making corrections for temperature and pressure changes and other variables usable, for example, to more closely control the fuel/air ratio at the burner and maximize the efficiency of the combustion process. Combustion gases may also be measured with this invention at other locations upstream of the actual stack discharge.

2. Background Art

Since most fuels of general interest are basically composed of carbon and hydrogen, the by products of combustion are primarily CO, $CO_2$ and $H_2O$. CO is the basic indicator of the incompleteness of the combustion process, since carbon oxidizes to $CO_2$ and under optimum conditions releases 14,500 BTU/lb. of carbon. The formation of CO only releases 4,350 BTU/lb. of carbon. $H_2O$ results, of course, primarily from combustion of hydrogen which releases 61,000 BTU/lb. of hydrogen. $H_2O$ is also present due to the humidity of the ambient combustion air and is contained within the fuel itself. As a result, the measure of CO, $CO_2$ and $H_2O$ provides a very good analysis of the combustion process. Oxygen ($O_2$) is also often used as an ancillary measurement as it is a good indicator of the theoretical excess air involved in the combustion process. The maximum combustion efficiency is obtained by minimizing excess air within the constraints of an acceptable level of CO. Thus, if it is possible to accurately measure the concentration of these different gases, it is also possible to adjust the combustion of the fuel so as to maximize the efficiency of the process. This has the advantage of reducing fuel costs and atmospheric pollution.

In the past, devices have been used where a source is provided on one side of the stack and a detector on the opposite side. The disadvantage of this type of device is that it is virtually impossible to calibrate such a device with a known gas and particularly it is not possible to do this at stack gas temperature and pressure. Further, the two sides must be carefully aligned and that alignment must be maintained. In addition, the gas dust content reduces the received radiation intensity which restricts the range of gas measurements. Therefore, it is only possible to get a zero concentration calibration check by shutting down the combustion process or creating simulated signals through additional sources or detectors to create an artificial zero and/or span (on) condition.

Some but not all of these difficulties have been overcome by the use of an optical sensing device having a probe extending into the stack from one side and including a chamber which can be permeated by the gas in the stack. The device is provided with optical means for detecting attenuation of light waves, such as infrared light waves, which are transmitted through the chamber and back again by means of a reflector for detection of the attenuation. These devices are an improvement of the across-the-stack devices in that the chamber can be purged of stack gases with a known gas or atmospheric air for running certain calibration checks and tests. However, heretofore the associated circuitry and apparatus has not been of sufficient sophistication of design to sense the presence of any one of a plurality of gases within the chamber and to accurately measure those gases without interference from co-existing gases and by adjusting for temperature and pressure variations within the stack.

DISCLOSURE OF THE INVENTION

In accordance with this invention a probe for receiving stack gases is provided. The probe includes a transceiver with optical means to sequentially and selectively project optic signals of different selected wavelengths into the probe and sense any attenuation of the signals due to presence of selected gases in the probe. A junction box (J-box) is connected to the transceiver to receive output signals from the transceiver representing the amount and type of gas in the probe. The J-box is also capable of running diagnostic tests on the probe and the transceiver. A remote control unit is connected to the J-box to process signals from the transceiver, compensate for the interference of co-existing gases, correct for temperature and pressure variations and provide readout of stack gas conditions and to run diagnostic checks.

More particularly, the transceiver provides an infrared chopped signal which can sense the presence of any one or all of CO, $CO_2$ and $H_2O$ gases. Power is provided to the transceiver and the remote control unit by the J-box. In addition, the J-box has means to purge the probe and transceiver for supplying known sample of gases to the probe for diagnostic purposes. These gases can be clean, dry atmospheric gas, $O_2$, CO, or $CO_2$. This is done by selectively providing the gases under pressure to the probe and transceiver to force the stack gases out of the probe. The J-box is conveniently attached to the outside of the stack adjacent to the transceiver. The remote control unit is located at a control station which may be some distance from the stack and includes a central processing unit (CPU), which processes the incoming signals from the transceiver and allow the operator to run the appropriate purging tests or obtain selective readings of the concentration of CO, $CO_2$ and $H_2O$, all of which have been corrected for interference effects and for any variations in temperature and pressure through the CPU.

Thus, with the present invention, tests can be made on the accuracy of the readings obtained from the probe and readings of the different gases can be obtained with high accuracy heretofore unknown. Although the detection of specific gases is described it will be understood that this invention can be used to detect other gases of interest, such as $N_2O$, $NO_x$, and $SO_2$.

Additional advantages of this invention will become apparent from the description which follows, taken in conjunction with the accompanying drawings.

BRIEF DESCRIPTION OF DRAWINGS

FIG. 2 is an enlarged longitudinal section through the probe and transceiver of FIG. 1;

FIG. 3 is an enlarged section, taken along line 3—3 of FIG. 2, showing details of a filter wheel;

BEST MODE FOR CARRYING OUT THE INVENTION

Figure 1:
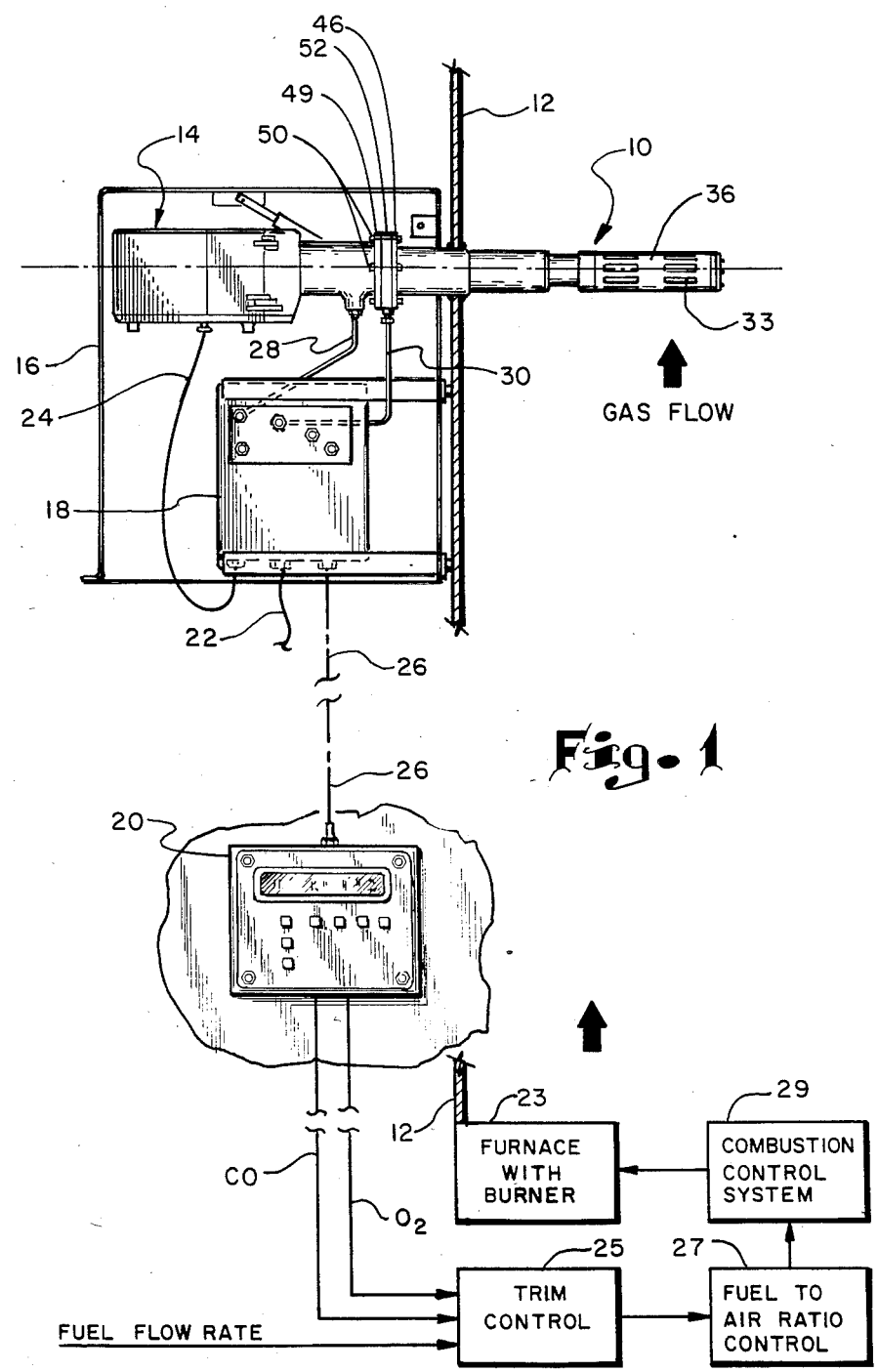
FIG. 1 is a side elevation of a multichannel combustion gas analyzer constructed in accordance with this invention, showing the attachment of the probe, transceiver and J-box to the side of a stack, a remote control unit at a distant location with outputs therefrom controlling the fuel-air mixture to a furnace burner.

In accordance with this invention, a gas probe 10 is provided which is mounted on and extends through stack wall 12. A transceiver 14 connected to the outer end of probe 10 and is mounted in housing 16 next to smoke stack 12. The housing also contains a junction box (J-box) 18. A remote control unit (RCU) 20, located at a different location, such as in a control room, completes the system. An outside power for the system is provided through AC line 22 to J-box 18 and RCU 20. The J-box in turn is connected through quick disconnect couplings, such as line 24, to the transceiver. The J-box is also connected to the remote control unit through line 26, as shown. As will be more fully described below, the J-box can be used for limited verification and testing procedures at the stack whereas the remote control unit 20 can be used for operating and testing and calibrating the probe under normal operating conditions. Pneumatic purge lines 28 and 30 also extend between the J-box and the transceiver and probe for purging the transceiver and probe of stack gases for testing the equipment against known gases, such as CO, $CO_2$ and $O_2$, for calibration and verification purposes. All of this is explained in more detail below.

The above described apparatus is shown in FIG. 1 as arranged for controlling the operation of a furnace with a burner 23 which emits the flue gases into the smoke stack 12. The remote control unit 20 has two output lines designated $O_2$ and CO with a fuel flow rate line providing input signals to a trim control 25. The output of the trim control is coupled to a fuel-to-air ratio control 27, which in turn regulates the combustion control system 29 of the furnace with burner 23. In this way the measured values of CO and $CO_2$ taken from the gases in the stack can be used to adjust the burner operation to maximize the efficiency of the combustion process in the furnace. $O_2$ or excess air is computed based on fuel characteristics and the indicated measurement values.

The probe 10, as shown in FIG. 2, includes a cylindrical ceramic filter 32 which forms an optical measurement cavity 34 therein and is surrounded by a gas flow deflector 36 which has openings therein as best seen in FIG. 1 for admitting the gases to the ceramic filter. The filter filters out any of the particulate material in the stack gases allowing only the flue or stack gases to pass through the filter and into optical cavity 34. Conveniently, the probe is typically five feet long which permits the measurement cavity 34 to be projected out into the flue gas stream away from the boundary layer wall effects of the stack. Optical cavity 34 includes a reflector 40 at its outer end and a lens 42 at the inner end. A gas temperature sensor such as a thermocouple 44 extends into the cavity as shown in FIG. 2 is connected to the circuitry of the transceiver, J-box and RCU to provide temperature readings of the flue gases within optical cavity 34 over a line 35. This information is input to the RCU to correct the other input data for temperature variations, all as described more fully below.

Advantageously, the probe is connected to a mounting flange 46 which projects through and is attached to the stack, as by welds 48. Transceiver 14 is also attached to flange 46 as by bolts 50 which extend through the flange as well as a plate 52 to hold the assembly together.

The optics are mounted in transceiver 14. An infrared light source 54, which is at a temperature of about 800° C., projects a beam of light through a series of lenses 56 and 58 and is reflected off of a beam splitter 60 after passing through a filter wheel 62. The filter wheel 62 is rotated by motor 64 at a speed, such as 12,000 rpm, to cause the light hitting the beam splitter to be chopped. Conveniently, the filter wheel, as best seen in FIG. 3 has five windows having different light transmitting characteristics. For example, window 66 is dark, i.e., non-light transmitting, whereas window 68 transmits 3.9 microns as a reference in that it simulates zero absorption for all light at a wavelength not absorbed by the gases of interest. Window 70 transmits light at 4.7 microns and is used for determining CO concentration in the gas. Window 72 transmits light at 3.3 microns and is used to determine the amount of $H_2O$ in the stack gas whereas window 74 transmits light at 4.5 microns to detect $CO_2$ gas in the stack. The selection of these particular wavelengths will be discussed more fully below.

Wheel 62 is provided with a plurality of peripheral notches 76 which are each opposite one of the windows and are sensed by a sensor 78 such as an LED photodiode with an electric output line 77, to identify which filter is located in front of light source 54. A sample and hold signal is derived from the filter wheel 62 and sensor 78 indicated by line 77 which is applied to a sequencer 81 in FIG. 6. The notches are smaller than their respective filters to allow for circuitry setting time. The sensor 78 allows signal integration through the open part of the notch. The signal is held outside of the notch. Opening 79, located just ahead of the notch 76 for dark filter 66 serves as a reset to set a counter in the sync circuit so that the adjacent notch will be recognized as the notch for dark filter 66.

Figure 6:
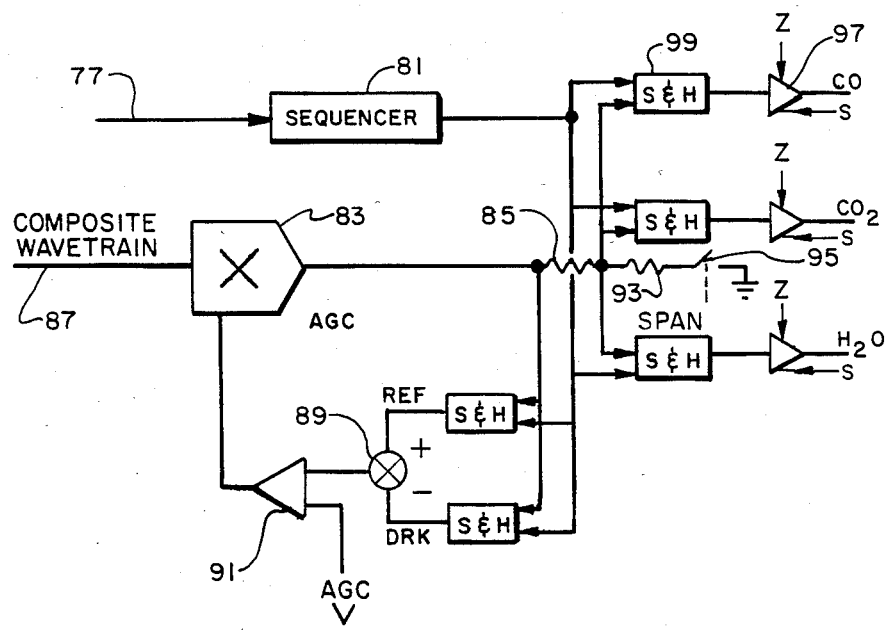
FIG. 6 is a block diagram of circuitry for the transceiver.

The light is reflected from the beam splitter 60 through an objective lens 80, through optical cavity 34 to reflector 40 and then back through the optical cavity, beam splitter 60 and through additional lenses 82 and 84 to detector 86 which as an electric output on line 87 is the form of a composite wavetrain that is applied to the transceiver circuitry shown in FIG. 6. While the light passes through the optical cavity 34, radiation is absorbed in a manner which is characteristic of the particular gases present. The detector senses the absorption present at each of the measurement channels, the dark channel which is total absorption, being used to eliminate background detector noise and drift.

Figure 4:
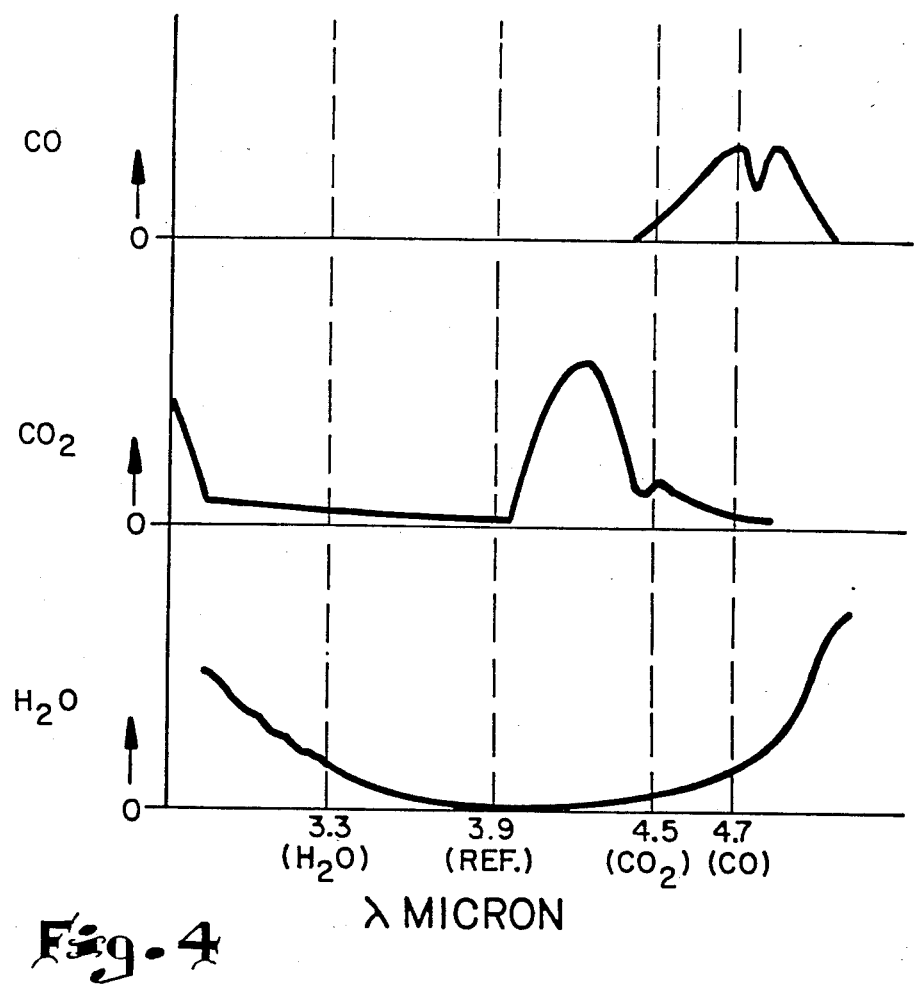
FIG. 4 are graphs showing the absorption of light at different wave lengths by CO, $CO_2$, and $H_2O$; at a specific temperature and pressure.

The absorption of CO, $CO_2$, and $H_2O$ at different wavelengths is shown in FIG. 4. Filter or window 70 passes light at 4.7 microns. As can be seen from FIG. 4, the attenuation of the light at this wavelength is much greater by CO gas than by either $CO_2$ or $H_2O$. Similarly, window 72 passes light at 3.3 microns. At this wavelength, $H_2O$ attenuates the signal much more than $CO_2$, and CO does not attenuate the signal at all. Finally, window 74 passes at the wave length of 4.5 microns where it can be seen that $CO_2$ attentuates the signal much more than either CO or $H_2O$. By appropriate mathematical representation and manipulation, these extraneous unwanted signals (interferences) can be removed to display accurate readings of the signals at the RCU 20.

FIG. 4 delineates the optical spectra for CO, $CO_2$ and $H_2O$ at a given temperature and pressure. Ideally, a burner control system will yield a high value of $CO_2$ concentration, typically 10–15%. However, $CO_2$ exhibits large absorption coefficient or high attenuation of the associated radiation intensity per unit of gas molecules. The ideal burner control system will maintain a low level of CO concentration, typically 100–500 ppm. CO exhibits a small absorption coefficient resulting in very little attenuation of the radiation of interest per unit of gas molecules. $H_2O$ appears in concentrations of 6–12% and exhibits small absorption coefficient.

Spectral filter wavelengths are chosen such that each full scale range will be compatible with the same measurement path length. The full scale range is further complicated through temperature affects on each absorption spectra. With the CO spectral filter located on the peak of the CO absorption spectra, CO will exhibit a negative overall temperature coefficient, yielding the low absorption coefficient even lower as temperature increases. Since $CO_2$ exhibits a large absorption coefficient, the $CO_2$ spectral filter cannot be located on the peak but must be located at a lower absorption point on the skirt of the $CO_2$ absorption spectra. However, location on the skirt will result in a positive overall temperature coefficient. The overall temperature coefficient is the combined effect of gas density and absorption coefficient variations with temperature. Utilizing a 71 cm optical cavity will result in compatible full-scale absorption at the worst case temperatures. Within this range of wavelengths is positioned the reference spectral filter. The reference filter is selected at a wavelength that is not absorbed by gas within a burner spectra. Any change in the reference intensity, then, will be caused by something other than spectral absorption of a gas. Such changes are variations in the lamp intensity or change in detector sensitivity. Changes in lens transmission due to temperature variations or surface contamination will also affect the reference channel. As the reference channel is attenuated, so will all other channels be attenuated and in the same proportion. In the present embodiment, it has been found to be desirable to keep the beam splitter at a temperature of approximately 125° F., the filter wheel at 165° F. and the detector at 32° F. by means of appropriate temperature control devices.

Figure 5:
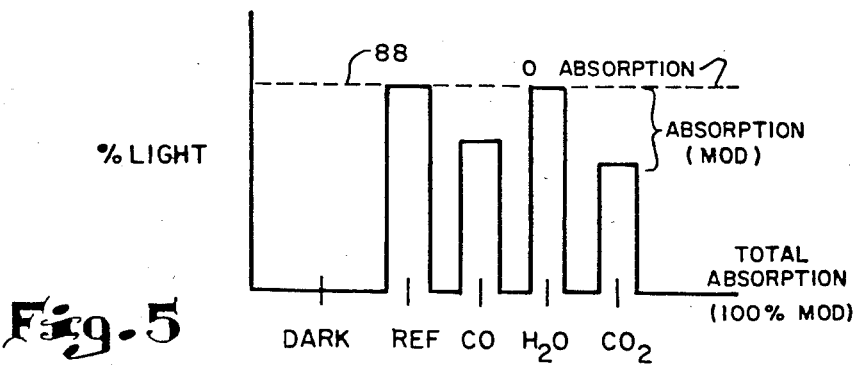
FIG. 5 is a graph showing relative absorption by the different filter segments in the filter wheel of FIG. 3.

The graph in FIG. 5 shows the attenuation of the light through the various filters. When the dark filter passes into the light beam, 100% of the light is absorbed (total absorption) whereas when the reference filter passes the light source 100% of the light at that wavelength is transmitted (zero absorption). The 100% transmission level or zero absorption is identified by dotted line 88. When the CO filter or window 70 passes the light, a portion of the light is absorbed as is indicated by the distance between line 88 and the top of the light bar shown in FIG. 5. Similarly, when window 72 passes there is almost no attenuation of the light and therefore the light bar approaches very close to the 100% absorption level of line 88. Finally, when window 74 passes, the signal will be attenuated considerably by the $CO_2$ gas present as noted by the distance between line 88 and the top of the $CO_2$ bar. The various attenuations are, of course, a function of the concentration of the gases present, optical path length and absorption coefficient as ideally or theoretically expressed in Beer's Law $I/I_o = e^{-abc}$ where a=absorption coefficient, b=path length, and c=concentration. Since Beer's Law is only valid for a single absorbing gas with a monochromatic interrogating light source, it is only useful for developing general theory. The specific system involved in this invention cannot be accurately described as a monochromatic system, and the characterization of absorption with respect to primary gas concentration, secondary or interfering gas concentrations, temperature and pressure results in an extremely non-linear set of data which is best described in tabular form. This is particularly important given the broad range of temperature over which the gases are measured, room temperature to 400° F. or 500° F.

The transceiver circuitry shown in FIG. 6 has signal processing electronics to which the composite waveform of FIG. 5 is applied which includes an automatic gain control circuit AGC including a multiplier 83, preferably comprised of an operational amplifier with a feedback loop. The composite wavetrain above described is applied to the input of the multiplier 83 over line 87 above described. In this circuit the output of the multiplier 83 is applied to a sample and hold circuit designated S&H for each of the references and dark channels and through an attenuating resistor 85 to sample and hold circuits designated S&H for each of the CO, $CO_2$, and $H_2O$ channels. Each of the sample and hold circuits receives an input signal from the sequencer 81. The sample and hold for the CO signal is designated by numeral 99 and this circuit is the same for each S&H block, although each channel obtains its sample at a different time corresponding to the filter wheel sequence illustrated in FIG. 5.

The outputs of the sample and hold circuits for the reference and dark signals are applied to a summer 89 which in turn applies the resulting difference signal to the input of an operational amplifier 91. A second input of this operational amplifier has the setpoint level of the AGC voltage (AGC V) applied thereto. The output of this operational amplifier 91 is applied to the input of the multiplier 83. A driver amplifier and manual potentiometer element is connected to the output of each sample and the hold for the CO, CO$_2$, and H$_2$O channels. The drive and manual potentiometer for the CO channel is designated by numeral 97 and this is the same element for each of the other CO$_2$ and H$_2$O channels. Z represents zero adjustment and S denotes span adjustment.

A span calibration check circuit is provided by the resistor 93 and switch 95 connected to ground. The resistor 93 has one side connected to the output side of the attenuating resistor 85.

The transceiver circuitry shown in FIG. 6 receives the composite wavetrain, normalizes the wavetrain to remove source, detector, and contamination variations, and provides continuous CO, CO$_2$, and H$_2$O electric current outputs for each channel. The outputs have not been corrected for temperature, pressure, interference or non-linearity effects.

The automatic gain control AGC circuit shown is used to normalize the composite wavetrain. This is accomplished by adjusting the gain of the input such that the reference to dark height is equal to the AGC voltage (AGC V). The remaining waveform will then be corrected by the same gain as required by the reference channel. Hence, if the source radiation deteriorates, the reference channel will drop, requiring an increase in circuit gain on all channels.

The normalized wavetrain is then sampled and held at each channel to provide a continuous output. Prior to sample and hold, each channel signal is zeroed by means of the manual potentiometer 97 in each of the CO, CO$_2$ and H$_2$O channels. The zero adjustment adjusts the height of a given channel to equal the height of the reference to dark signal. This is a channel gain adjustment to zero the channel. The difference between the reference and a channel signal height represents the percent modulation of that channel. The difference is adjusted to zero only when zero gas is in the measurement cavity. The difference is sampled and held to obtain a continuous output.

An electro/optic calibration is provided using resistor 93 and switch 95. This calibration will provide a known attenuation, or percent modulation, for each channel. The attenuator, shown in FIG. 6, is actuated by the circuit ground via resistor 93 and switch 95. Span occurs when the measurement cavity is purged with zero gas. The attenuator is set up to yield full scale outputs with zero gas. If the cell is not properly purged, the gas remaining in the measurement cavity will add to the full scale modulation on the respective channel.

Figure 7:
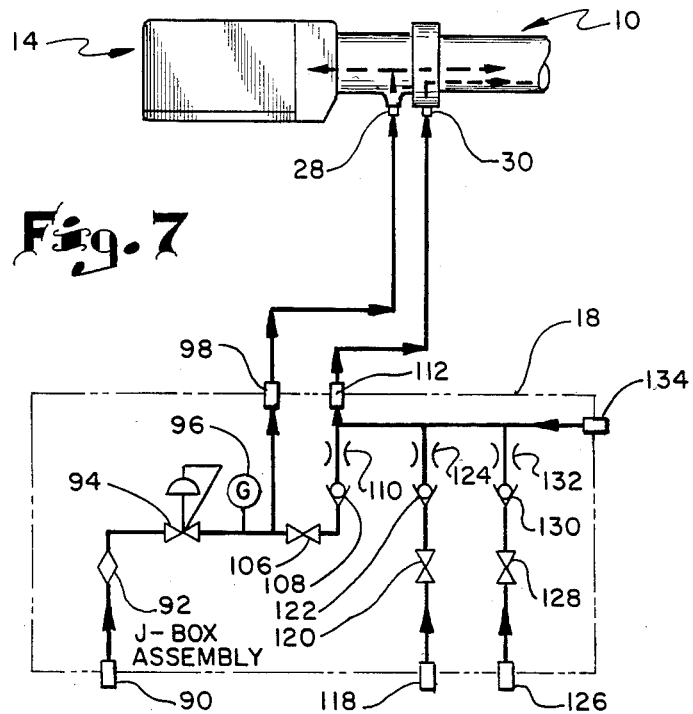
FIG. 7 is a diagram of the pneumatic system within the J-box for purging the probe and transceiver of stack gases.

The purging system is best understood by reference to both FIGS. 2 and 7. As seen in FIG. 7, clean dry air can be supplied to J-box 18 through coupling 90 at approximately 70 to 100 psi. The air passes through a filter 92 and a pressure reducing valve 94, which reduces the pressure to 5 psi, through gauge 96 and coupling 98 which is connected to line 28 extending into the transceiver. As best seen in FIG. 2, line 28 goes into the transceiver and is connected to a T-connection 100 having a rearwardly extending line 102 connected to one side and to supply purging gas to the transceiver and a forwarding extending line 104 to provide purging gas to the portion of the probe to the left of field lens 42. Flow rate is controlled via a critical orifice on each side of the T-connection 100. Conveniently, field lens 42 may be provided with a sealing means such as an O-ring (not shown) to isolate the optical cavity 34 from the rest of the system. The purging gas runs through the transceiver and the left hand portion of the probe continually to keep these areas free of stack gases and any other contaminated gases so that the transmission of light from source 54 will not be attenuated by unwanted and unknown gases and therefore give false signals. Conveniently, the total optical path length in the probe is four times the length of the optical cavity 34 while the transceiver path length is equal to the length of optical cavity 34. Therefore, any moisture or hydrocarbons in the purged air will generate five times the signal level as would be measured in the measurement cavity alone.

When it is desired to purge the optical cavity 34 of stack gases, solenoid valve 106 will be activated to allow dry air at 5 psi to pass through check valve 108, restricted orifice 110 and coupling 112 to purge line 30. Referring to FIG. 2, line 30 is connected to a purge line 114 which runs past lens 46 to an orifice 116 for admitting purge air into optical cavity 34. Thus, when solenoid 106 is open the purge air admitted into cavity 34 will force the stack gases through ceramic filter 32 thereby clearing cavity 34 of these stack gases so that a check of the system can be made free of stack gas background effects.

Conveniently, a second coupling 118 on J-box 18 can be connected to a source of CO so that if it is desired to run a test for CO gas in optical cavity 34 solenoid valve 120 may be open to allow the gas to pass one-way check valve 122, restrictor 124 and coupling 120 into line 30 as described previously with respect to the purge gas. Of course, when CO is admitted to the system check valve 106 will be closed so that no air will be admitted to optical cavity 34. Similarly, CO$_2$ can be provided through coupling 126 when check valve 128 is open so that the CO$_2$ can flow through a one-way check valve 130 and restriction 132 and then via coupling 112 to purge line 30. In this way the response of the entire system can be checked with a known gas at stack measurement temperature and pressure, without additional sources or detectors.

It can be seen, that dry air, CO or CO$_2$ can be selectively supplied to the optical cavity 34 whenever calibration checks are desired. This can be done once a day, once per hour or on any other more or less frequent basis, as the particular installation requires. A further coupling 134 is provided in J-box 18 as shown for manually providing the gases through coupling 112 and to purge line 30 if it is desired to make the checks on a manual basis rather than automatically through the respective solenoid valves 106, 120 and 128. Of course, will be understood that these solenoid valves are controlled either from the J-box or the RCU by the operator.

Figure 8:
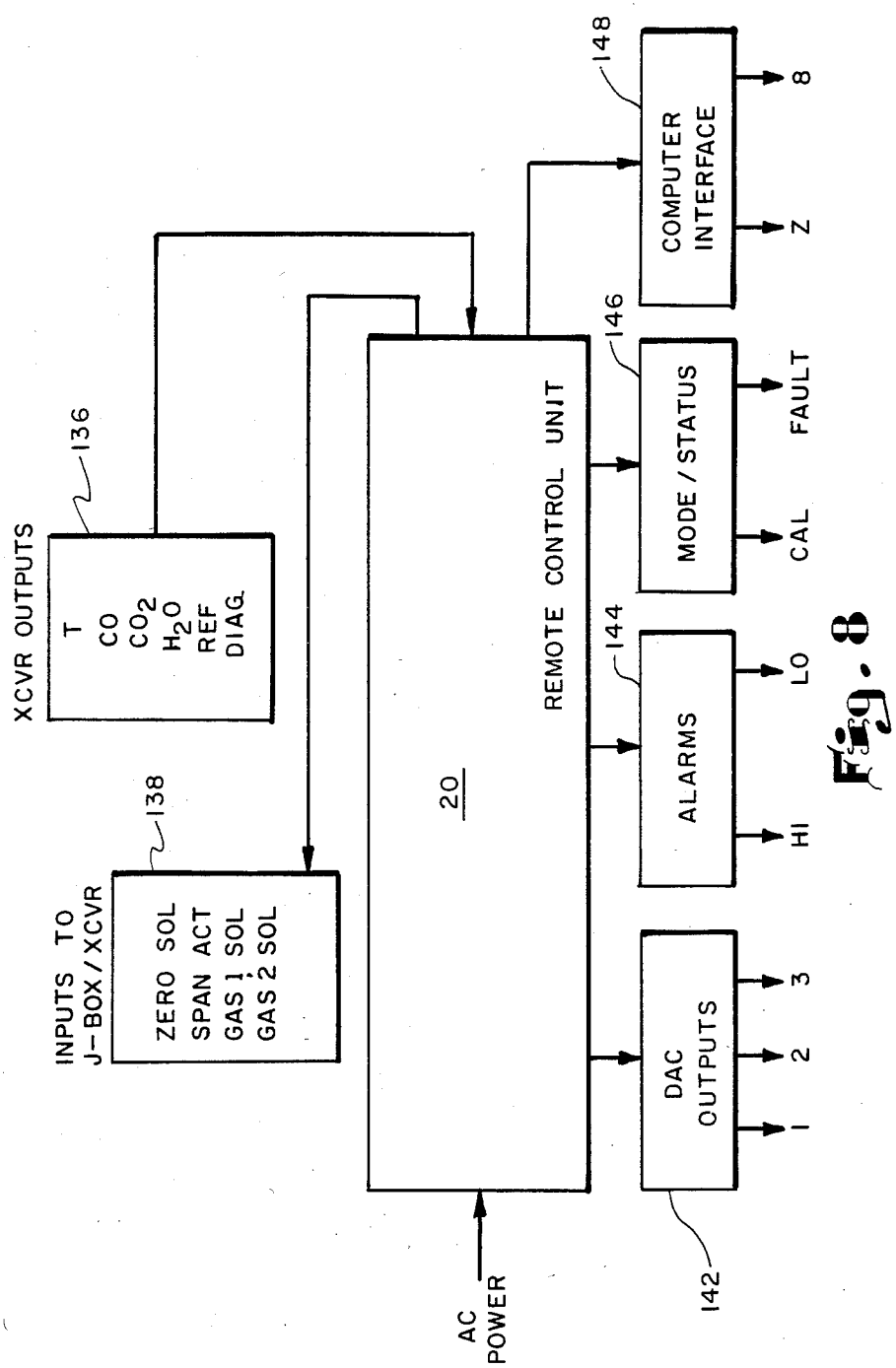
FIG. 8 is a block diagram showing the inputs to and outputs from the remote control unit.

Referring now to FIG. 8, the general block diagram shown collectively identifies the transceiver outputs in block 136 which are input into the remote control unit 20 and collectively identifies the inputs to the J-box and transceiver from the remote control unit in block 138. The remote control unit has output blocks 142, 144, 146 and 148 identified as DAC outputs, alarms, mode/status, and computer interface, respectively.

Figure 9:
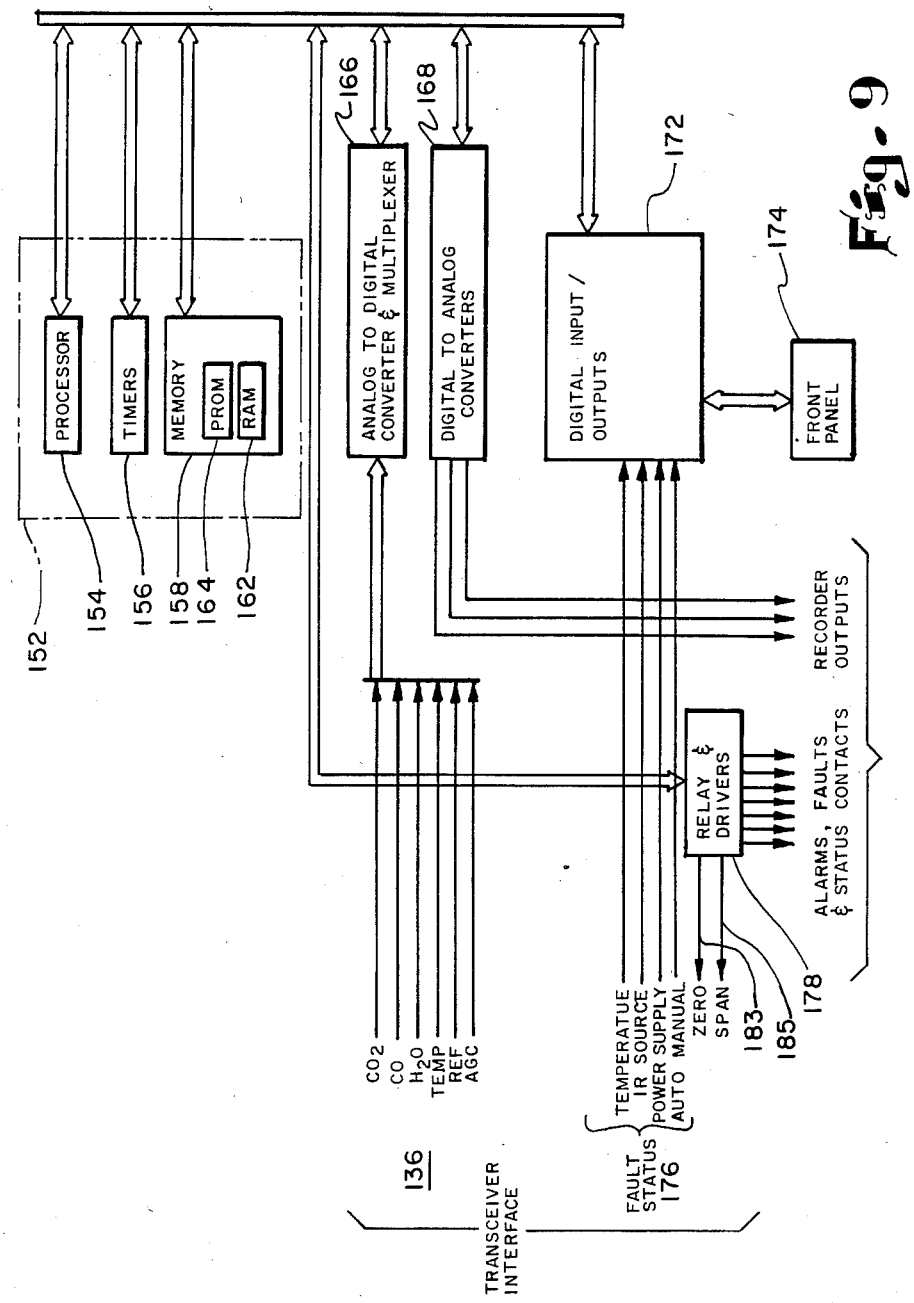
FIG. 9 is a block diagram of the circuitry of the remote control unit.

A block diagram depicting the remote control unit is shown in FIG. 9. The apparatus shown includes a digital central processing unit (CPU) 152 having a processor 154, timers 156, and a memory 158 with the required RAM 162 and PROM 164 storage. An Intel i SBC 80/24 providing an 8085 CPU, 4K bytes of RAM and 32K bytes PROM, and an RS 232 serial port for use with the displayer and timers is apparatus suitable for this purpose.

The transceiver outputs 136, in current measurements, are applied to an analog-to-digital converter and multiplexer 166, from which the converted data is entered into the CPU.

Outputs from the CPU are applied to digital-to-analog converters 168 which in turn provide three recorder analog outputs.

Outputs from the CPU are also applied to a digital input/output terminal 172 for display by a front panel 174. The front panel is, for example, a TM70 or TM76 alphanumeric keyboard and display.

Advantageously, a number of status faults, collectively identified as numeral 176, are input into the digital input/output terminal 172. A plurality of relays and drivers 178 receive data from the CPU to alarms, faults, and status contact outputs. In addition, a zero output and a span output 183 and 185, respectively, are derived from the relays and drivers 178.

During operation, the analog data from the transceiver is converted to a digital form by converter 166 and stored in the CPU 152. The CPU is programmed to convert the outputs related to gas measurements to percent modulation and make a number of corrections described herein and the output data relative to the measurements is converted to an analog signal by converter 168 and presented as three recorder outputs as shown. The CPU in general communicates in parallel with the other apparatus shown in FIG. 9.

Figure 10:
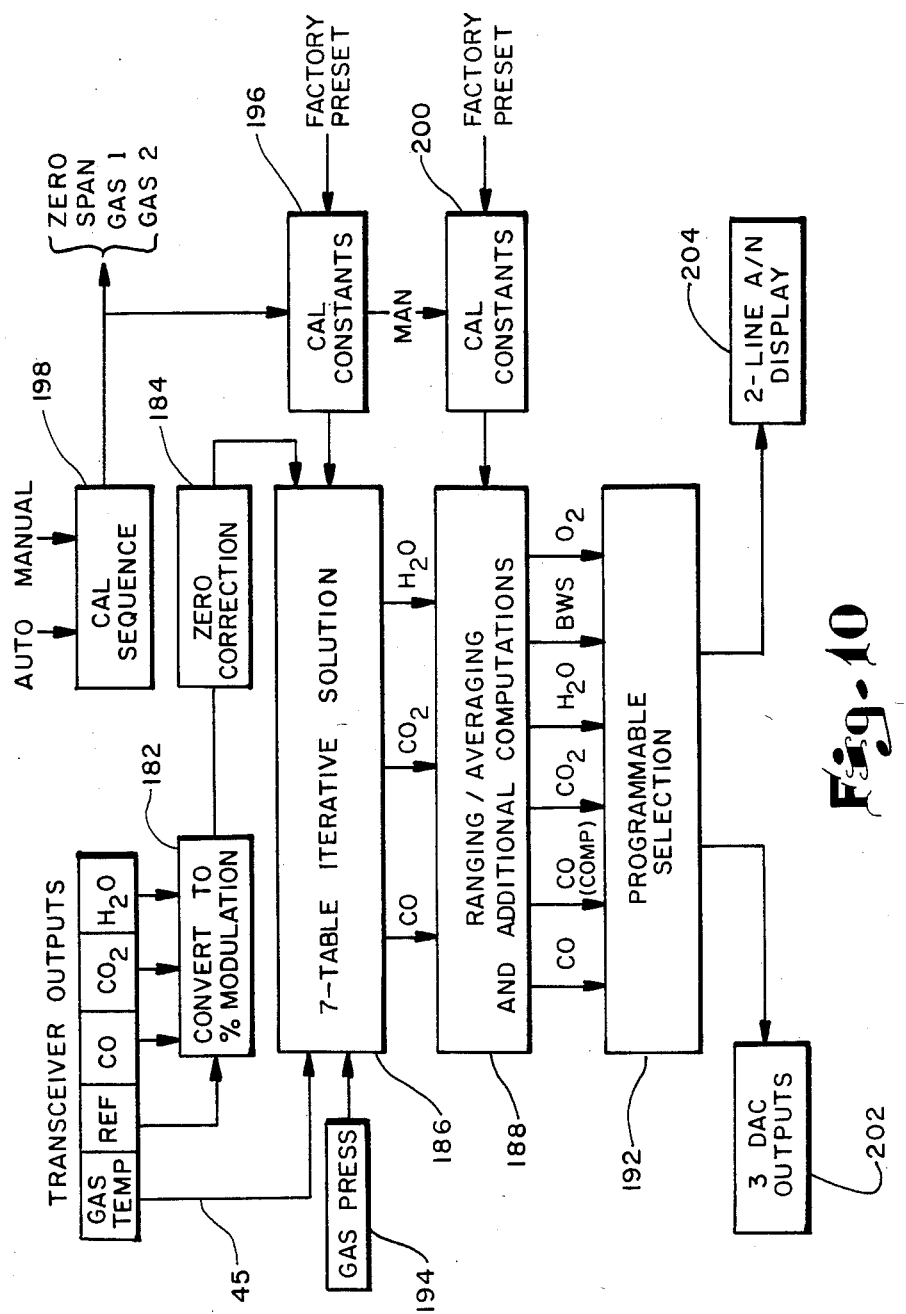
FIG. 10 is a computational block diagram of the CPU and related inputs for the remote control unit.

The functions performed by the programmed CPU will now be further explained, first with reference to the computational block diagram shown in FIG. 10. The functions or operations carried out by the computer are represented in blocks 182, 184, 186, 188, and 192 with identifying word explanations.

The transceiver outputs GAS TEMP, REF, CO, $CO_2$ and $H_2O$, which are current outputs, are converted to a percent modulation value in block 182 and a zero correction is carried out in block 184 prior to entry into block 186. Block 186 is identified as 7-table iterative solution. In block 186 pressure, temperature, interference and linearity are compensated for, as described more fully hereinafter with reference to FIGS. 11 and 12. Gas temperature taken from the probe is applied over line 45 above described. Other inputs to block 186 are a standard gas pressure indicated by block 194 and a calibration constant represented by block 196. A calibration sequence block 198 with either automatic or manual control, provides inputs to the calibration constant with block 196.

Corrected outputs in ppm CO, %$CO_2$ and $H_2O$ are input from block 186 into a block 188 identified as ranging/averaging and additional computations. In block 188 table outputs CO, $CO_2$ and $H_2O$ are averaged. One of the additional computations carried out in block 188 is a compensated CO measurement value equal to $$CO \text{ measured} \times \frac{CO_2 \text{ stiochiometric}}{CO_2 \text{ measured}}$$

that is insensitive to the dilution effects of excess air.

Another computation carried out in block 188 is an efficiency measurement value %CE=%CE Dry flue gas $\times$ %CE combustibles $\times$ 1/100 where:
%CE Dry flue gas = $K_1[(0.964+0.000135\%$ EA$)-(0.000207+1.68\times10^{-6}\times\%$EA$)$ $T_s]$ 100
$T_s$ = flue gas exit/stack temperature °F.

$K_1$ = fuel sensitivity factor; oil = 1.0, Natural gas = 0.91

$$\% EA = \text{Excess air} = \left(\frac{20.9}{20.9 - \% O_{2D}} - 1\right) 100$$

% $O_{2D}$ = % dry oxygen $$\% CE \text{ Combustibles} = \left[1 - \frac{0.00028 \times CO}{100} K_2\right] 100$$

$K_2$ = Ratio of total heat loss to all unburned combustibles to that only due to CO, ideally unity.
CO = ppm of carbon monoxide corrected to dry basis stiochiometric conditions A calibration constant block 200 provides a calibration input to block 188. A data base of the results, along with computation required for control systems and compliance monitors are made available for operator selection by the programmable selection block 192 to either the three DAC outputs represented by block 202 or a two-line alphanumeric display represented by block 204.

The primary signal conditioning is carried out by the CPU in the percent modulation calculations. These calculations convert the milliamps from the transceiver to percent modulation. The calculations result in data smoothing, zero correction, and corrections for reference variations.

The smoothing results when all milliamp readings are averaged for five seconds prior to entering the percent modulation calculations. Zero correction results from using the two-minute averaged zero value retained from the last zero calibration sequence. This zero represents a 0% modulation vs. milliamp line. The span or 100% modulation is represented by the current 5 sec. reference average times a full scale value for each channel.

Given these points for each measurement channel, the percent modulation calculation is simply a straight line equation which can vary as either the span varies or as the zero calibration value changes. The results of the percent modulation calculation are $H_2O$ % Modulation, $CO_2$ % Modulation and CO % Modulation.

Figure 11:
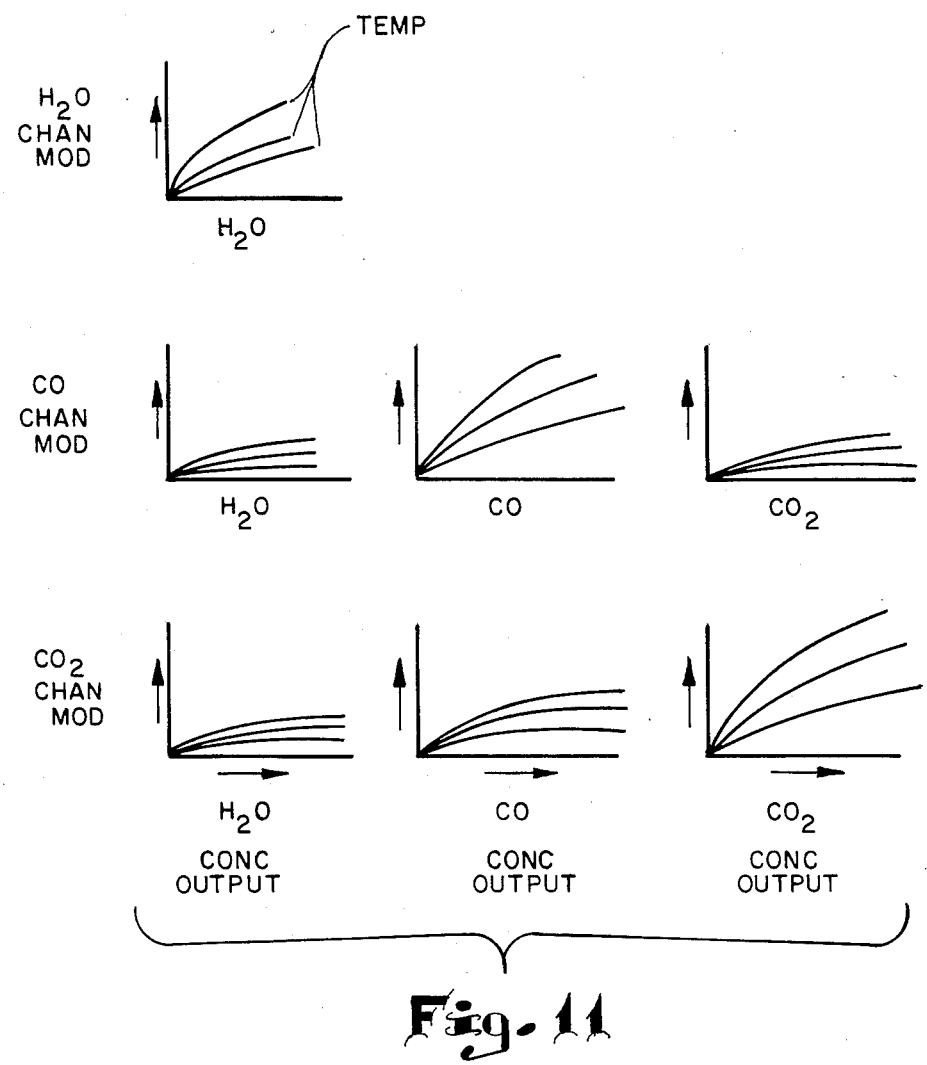
FIG. 11 is a series of seven curves, each showing channel percent modulation, with respect to concentration output for $H_2O$, CO, and $CO_2$ gases at different temperatures.

Block 186 will now be further explained with reference to FIG. 11, showing seven tables in which each curve shown represents a channel % Modulation with respect to concentration for a family of temperatures. Prior to entering the tables, each percent modulation is corrected for measurement pressure to reference the measurement pressure to sea level. CO and $H_2O$ are modified by multiplying percent modulations by 760/Pressure, where the pressure is manually inserted by mmHg. The $CO_2$, derived from a linear least-square solution to physical data, s 1000/Pressure+240. Temperature is linearized through a simple table.

Since the $H_2O$ spectral filter has been selected at a wavelength that is not interfered by either CO or $CO_2$, the %$H_2O$ modulation is the first to be interpolated in the $H_2O$ CHAN MOD vs. $H_2O$ concentration table. The first interpolation will be at a nearest, but lower, % Modulation that is tabulated temperature points for the measured temperature point. Similarly, the nearest, but higher, % Modulation that is tabulated will be temperature interpolated. These two points represent the nearest points above and below the desired modulation at the desired temperature. The final interpolation, then, is for the active concentration for the measured % modulation between these two points. The interpolation for all curves is the same as above and will be only connoted as interpolated.

Given the $H_2O$ concentration, the CO and $CO_2$ interference due to $H_2O$ can be determined. Entering the CO CHAN Mod and $CO_2$ CHAN MOD vs. $H_2O$ concentration tables, respectively, the % Modulation caused by $H_2O$ concentration can be interpolated. These % Modulations are then subtracted from the modulations derived from the respective CO and $CO_2$ channels.

Since CO and $CO_2$ mutually interfere with each other, the final solution must be of an iterative nature. To determine the CO interference upon $CO_2$, the previous concentration of CO is used to interpolate the $CO_2$ CHAN MOD caused by CO. Similarly, the CO CHAN MOD caused by $CO_2$ is determined using previous concentrations of $CO_2$. These interfering modulations are subtracted from the modulations already corrected for $H_2O$ interference. Then the values of CO and $CO_2$ are refined in an interative manner until the residuals or errors are of negligible size.

With regard to calibration, the seven curves, rudimentarily illustrated in FIG. 11, may be developed using analog curve fitting techniques. The CPU obtains the same results digitally, by storing empirically derived data points within the stored program. The seven curves of gas concentration output v. % Modulation for the three measured gases, each recorded at from five to seven different temperatures, are tabulated and stored in PROM in the CPU. The stored program linearly interpolates between neighboring data points to obtain the required measurement point on each curve. The number of data points stored is selected to best fit the curvature of each respective curve.

The data points are empirically measured by placing a known concentration of gas at a known temperature into the measurement cavity and recording the required output of the transceiver in a % Modulation. A standard gravimetric standard gas is diluted with nitrogen by means of a gas divider to obtain the desired concentration ranges. The measurement cavity is heated to the desired gas temperature utilizing a good quality temperature controller. Thus, the response of each measurement channel is recorded for each gas of interest over the range of specified temperatures.

The manually activated Dynamic Calibration stored program will first obtain good zeros for establishing accurate % Modulations. Then, assuming that the optional automatic calibration assembly is installed in the J-box, a customer supplied CO gas will be activated into the measurement cavity. The stored program will then determine a gain factor (COS) that must be applied to the CO concentration of the CO CHAN MOD vs. CO concentration table to make the final iterative interpolated solution agree with the gas value entered by the customer (COG). After the CO gas measurement is complete, about two minutes, the $CO_2$ gas is sequenced into the cavity. In a manner similar to the CO, the $CO_2$ gain factor $CO_2S$ is altered for agreement with the customer entered $CO_2G$. To activate the correction, the equipment operator must manually accept the corrections computed and displayed by the RCU.

The resulting linearized CO, $CO_2$, $H_2O$ and temperature, along with calculated values for dewpoint, $O_2$, BWS (stack moisture), and CO-ST (CO compensated for air leakage), are all available as output from block 192 for selection as three recorded outputs.

The readouts can be configured through the front panel to display any combination of CO, $CO_2$, $H_2O$, TEMP., CO-ST, BWS and $O_2$, or test functions REF. and AGC.

Figure 12:
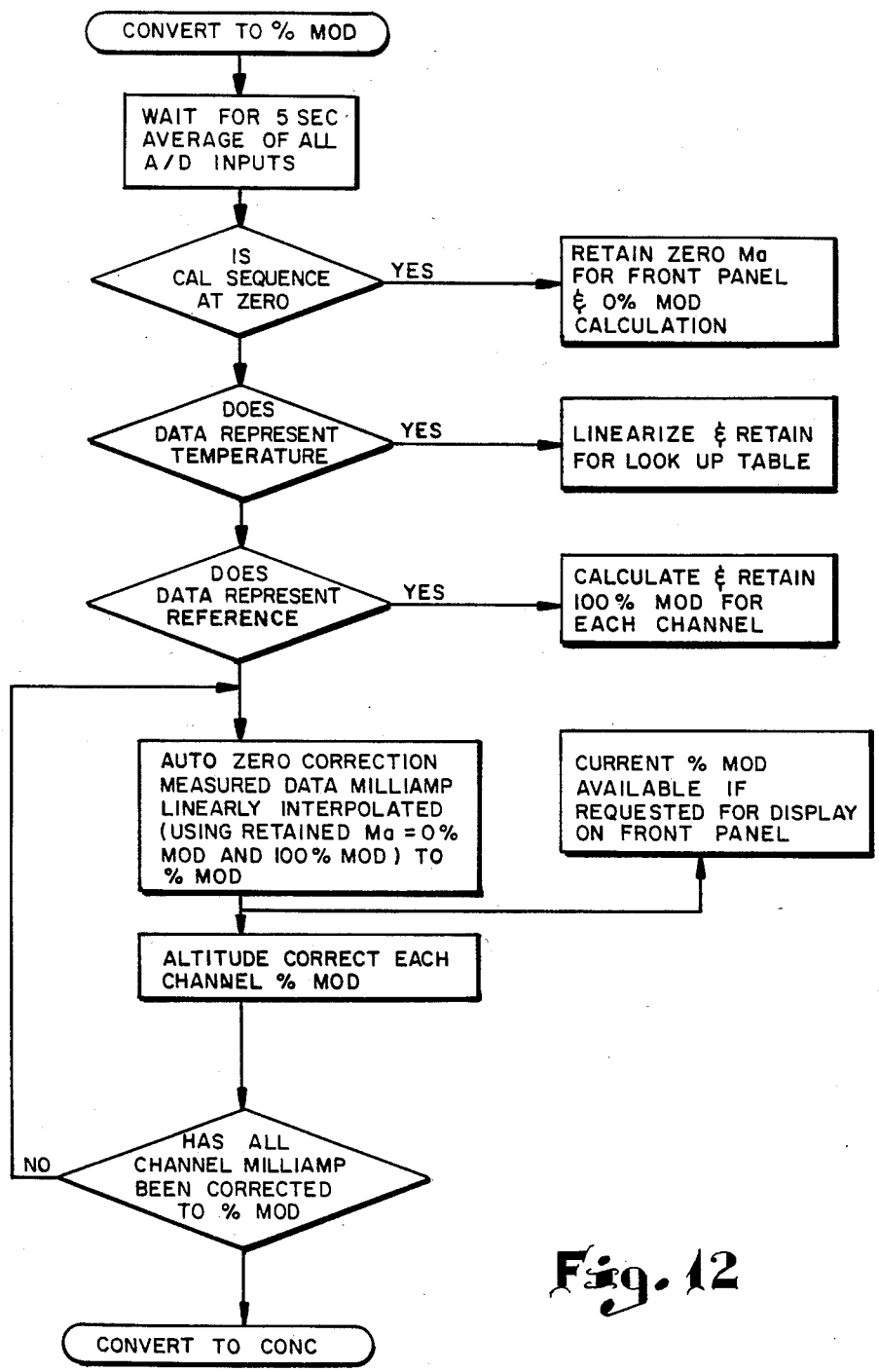
FIG. 12 is a flow chart of the program for the remote control unit from convert to percent modulation to convert to concentration.
Figure 13:
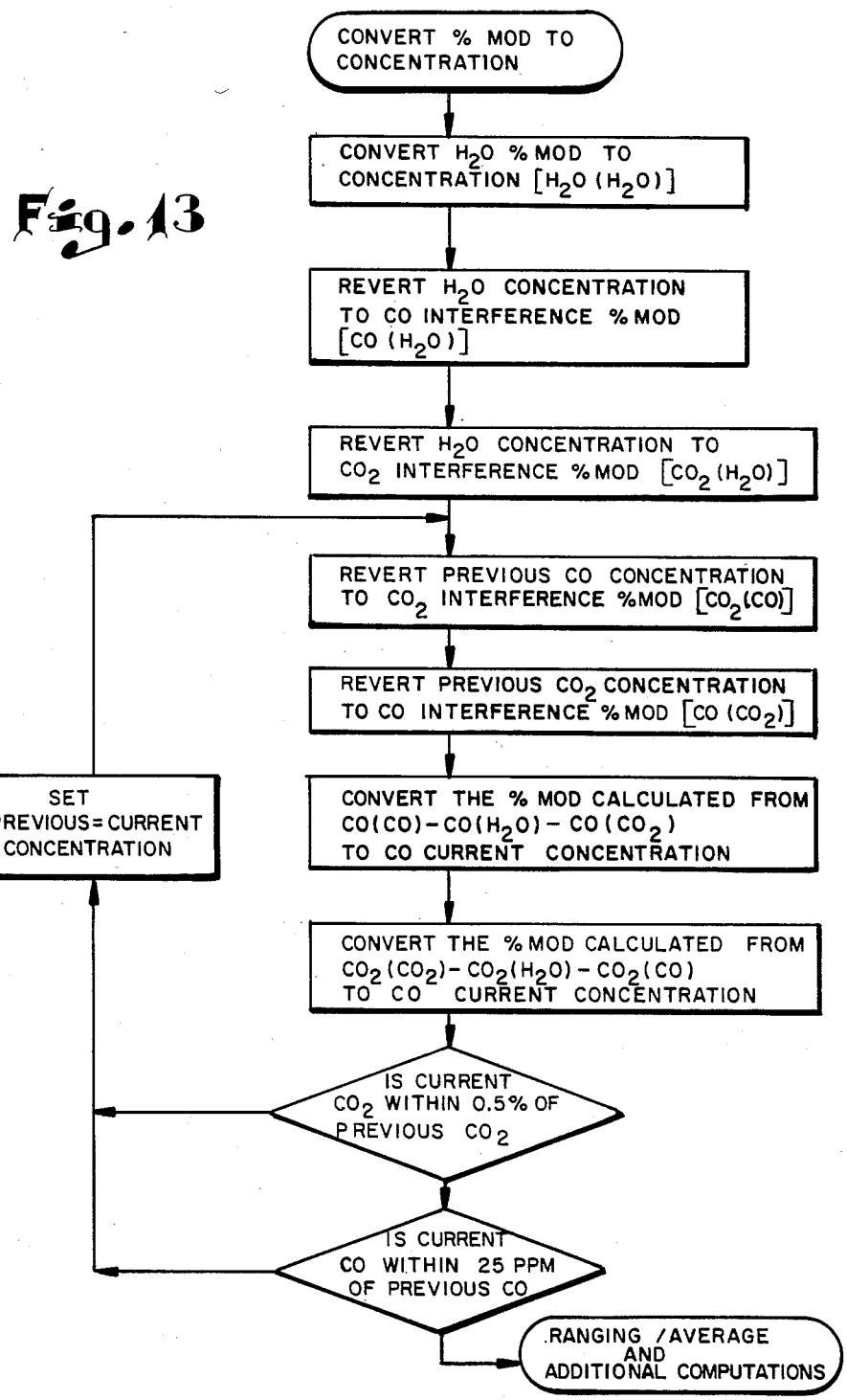
FIG. 13 is a flow chart of the program for the remote control unit from convert to concentration to ranging-/average and additional computations.
Figure 14:
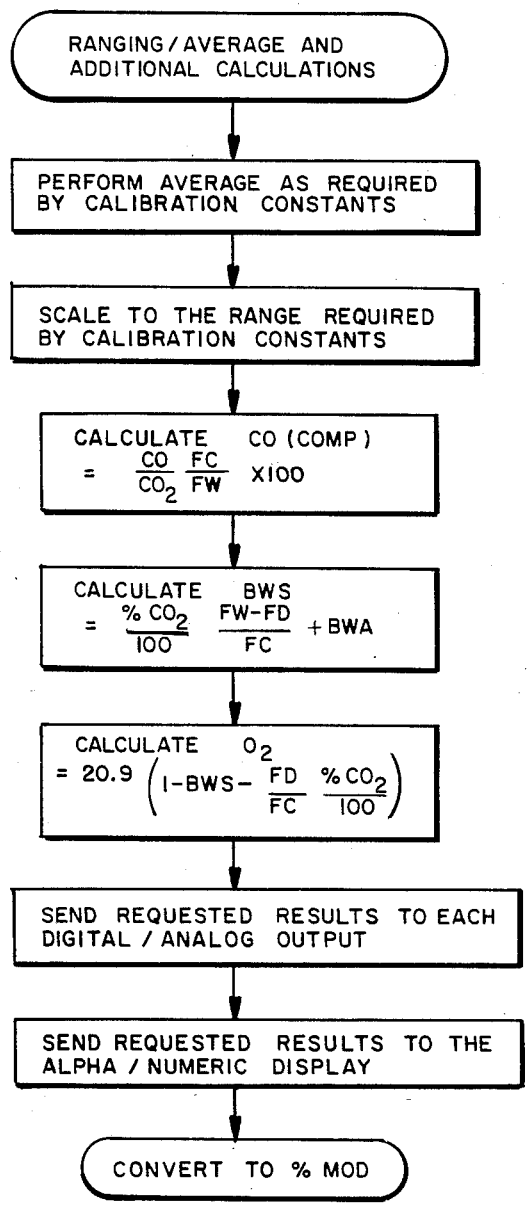
FIG. 14 is a flow chart of the program from ranging-/averaging and additional calculations to convert to percent modulation.
Figure 15:
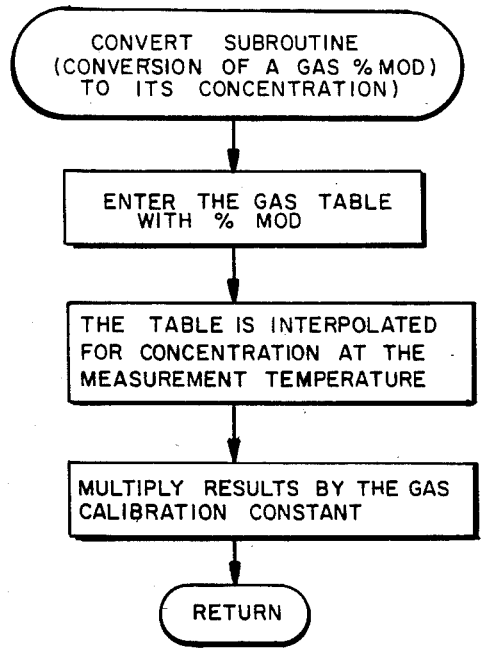
FIG. 15 is a flow chart of the program from convert subroutine to its concentration to return.
Figure 16:
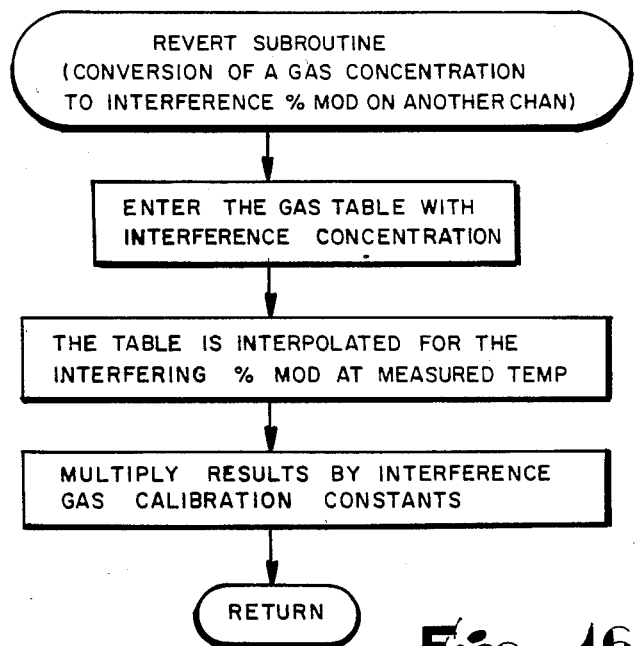
FIG. 16 is a flow chart of the program from convert subroutine to return.

A flow chart of the program for the CPU as above described, to convert to percent modulation to concentration and from concentration to output, is illustrated in FIG. 12. In this chart CO (CO) denotes the CO transceiver output read with CO concentration. CO ($CO_2$) denotes the CO output read with $CO_2$ concentration. CO ($H_2O$) denotes CO output with $H_2O$ concentration. Similarly, $CO_2(CO_2)$, $CO_2(CO)$, $CO_2(H_2O)$ denotes the $CO_2$ transceiver output read with $CO_2$, CO, then $H_2O$ concentrations, respectively, in the measurement cavity.

Other industrial applications for the above described apparatus include the monitoring of $H_2O$ for controlling of the water flow rate in a quenching machine, to monitor CO and using this to ensure complete combustion of hazardous waste material, for monitoring $CO_2$ to adjust measured pollutant for diluent air in EPA air compliance monitoring applications involving large fossil fuel fired steam generators, monitoring $H_2O$ for diagnostic purposes in boiler maintenance (steam tube leaks and burner condition) and for monitoring $H_2O$ in drying processes to increase energy efficiency. Combining all the measured parameters CO, $CO_2$, $H_2O$ with an oxygen measurement permits a determination of fuel composition factors.

The invention has been described in detail with particular reference to preferred embodiments thereof, but it will be understood that variations and modifications can be effected within the spirit and scope of the invention.

We claim:

1. Apparatus for measuring multiple component interfering gases contained in flue gases issuing from a stack due to combustion, comprising:
   a probe for mounting to extend through the wall of a stack including a measurement cavity through which combustion gases in the stack can pass;
   a transceiver mounted to said probe externally of said stack including an optical means and electric circuit means,
   said optical means having a chopped light source for projecting a succession of beams of light of different selected wavelengths one at a time into said probe, a detector for continuously detecting any attenuation of each of the light beams by said gases in said probe for providing a measure of the extend of absorption of each gas of interset in each of a plurality of separate channels, and a zero absorption channel providing a reference for the other channels,
   said electric circuit means providing an electric output representing each of said absorption measurements; and
   control means coupled to said transceiver including first means for continuously converting said electric output to a corresponding percent modulation output for each of said gases of interest, for continuously correcting each of said percent modulation outputs for temperature, of correcting each of said percent modulation outputs for pressure, for correcting said percent modulation output for interference between measured gases, and to provide corrected continuous outputs representing the concentration of each of said measured gases, said control means including automatic calibration means for continuously purging said measurement with dry air to provide zero values that are used in calculating said percent modulation and means to couple a gas valve into said measurement cavity for the purpose of obtaining a gain factor for continuously correcting the measured results.

2. Apparatus as set forth in claim 1 wherein said measured gases are CO, $CO_2$ and $H_2O$.

3. Apparatus as set forth in claim 1, wherein said electric circuit portion includes an automatic gain control to normalize said output signal from said detector to remove source, detection and contamination variations.

4. Apparatus as set forth in claim 1, wherein said percent modulation output is defined as $100(1-I/I_o)$ I=light remaining after attenuation, $I_o$=total available light.

5. Apparatus as set forth in claim 1, including a junction box mountable on said stack adjacent said transceiver electrically coupled to said transceiver and arranged to transfer transceiver outputs to said control unit and control unit outputs to said transceiver.

6. Apparatus as set forth in claim 1, including means for displaying said corrected outputs.

7. Apparatus as set forth in claim 1, including means for converting said corrected outputs to selectable digital-to-analog converter recorder outputs.

8. Apparatus as set forth in claim 1, including means for using selected of said corrected outputs from said control means to adjust the fuel/air ratio to the burner of a furnace to maximize the efficiency of the combustion process in the furnace.

9. Apparatus for measuring multiple component interfering gases contained in flue gases issuing from a stack due to combustion, comprising:
a probe for mounting to extend through the wall of a stack including a measurement cavity through which combustion gases in the stack can circulate;
a transceiver mounted to said probe externally of said stack including an optical portion and an electric circuit portion,
said optical portion having a light source and a rotary filter wheel with a narrow band filter corresponding to the primary absorption wavelength of each gas of interest for a selected number of separate gas measurement channels, a reference channel, and a total absorption channel, for projecting a succession of beams of light of different selected wavelengths one at a time into said probe, and a detector for continuously detecting any attenuation of the light beams by said gases in said probe for providing a measure of the extend of absorption of each gas of interest in each of said channels, said total absorption channel eliminating background noise and drift and said zero absorption channel providing a reference for the other channels,
said electric circuit portion providing an electric output representing each of said absorption measurements; and
a control unit coupled to said transceiver including first computing means for continuously converting said electric output to a corresponding percent modulation output for each of said gases of interest and second computing means for continously correcting each of said percent modulation outputs for temperature, for correcting each said output for pressure and moisture, for correcting said percent modulation output for interference between measured gases, for correcting said percent modulation output for non-linearity, for calibrating, ranging and averaging each of said percent modulation outputs, and to provide corrected continuous outputs representing the concentration of each of said measured gases,
said control unit including an automatic calibration means for continuosly purging said measurement with dry air to provide zero value that are used in calculating said percent modulation and means to couple a gas valve into said measurement cavity for the purpose of obtaining a gain factor for continuously correcting the measured results.

10. Apparatus as set forth in claim 9, wherein said transceiver includes sample and hold means to produce a sample and hold signal from said filter wheel to sample and hold a normalized signal for each of said channels.

11. Apparatus as set forth in claim 10, wherein said sample and hold means includes a notch in said wheel opposite each filter sensed by a sensor to identify which filter is opposite said light source.

12. Apparatus as set forth in claim 10, wherein said light source emits infrared radiation from an electrically heated metallic source through said rotating filter wheel with filters defining said separate channels, said radiation being directed onto a beam splitter which reflects the beam down the probe through a measurement cavity, the radiation being absorbed in a manner characteristic of the gases present.

13. Apparatus for measuring multiple component interfering gases contained in flue gases issuing from a stack due to combustion, comprising:
a probe for mounting to extend through the wall of a stack through which combustion gases in the stack can pass;
a transceiver mounted to said probe externally of said stack including an optical means and electric circuit means;
said optical means having a chopped light source for projecting beams of light of different selected wavelengths into said probe, a detector for detecting any attenuation of the light beams by said gases in said probe for providing a measure of the extend of absorption of each gas of interest in each of a plurality of separate channels, and a zero absorption channel providing a reference for the other channels,
said electric circuit means providing an electric output representing each of said absorption measurements; and
control means coupled to said transceiver including first means for converting said electric output to a corresponding percent modulation output for each of said gases of interest, for correcting each of said percent modulation outputs for temperature and pressure, for correcting said percent modulation output for interference between measured gases, and to provide corrected outputs representing the concentration of each of said measured gases,
said control means including a programmed digital computer using a table iterative solution having channel percent modulation with respect to gas concentration output for a family of temperatures of each of said measured gases.

14. Apparatus as set forth in claim 13, wherein said measured gases are $H_2O$, CO and $CO_2$ and a seven-table iterative solution is used in said control unit.

15. Apparatus for measuring multiple component interfering gases contained in flue gases issuing from a stack due to combustion, comprising:

a probe for mounting to extend through the wall of a stack through which combustion gases in the stack can pass;

a transceiver mounted to said probe externally of said stack including an optical means and electric circuit means, said optical means having a chopped light source for projecting beams of light of different selected wavelengths into said probe, a detector for detecting any attenuation of the light beams by said gases in said probe for providing a measure of the extend of absorption of each gas of interest in each of a plurality of separate channels, and a zero absorption channel providing a reference for the other channels, said electric circuit means providing an electric output representing each of said absorption measurements; and control means coupled to said transceiver including first means for converting said electric output to a corresponding percent modulation output for each of said gases of interest, for correcting each of said percent modulation outputs for temperature and pressure, for correcting said percent modulation output for interference between measured gases, and to provide corrected outputs representing the concentration of each of said measured gases, said control means providing a compensated CO measurement value equal to $$CO\ measured \times \frac{CO_2\ stiochiometric}{CO_2\ measured}$$

that is insensitive to the dilution effects of excess air.

16. Apparatus for measuring multiple component interfering gases contained in flue gases issuing from a stack due to combustion, comprising:

a probe for mounting to extend through the wall of a stack through which combustion gases in the stack can pass;

a transceiver mounted to said probe externally of said stack including an optical means and electric circuit means, said optical means having a chopped light source for projecting beams of light of different selected wavelengths into said probe, a detector for detecting any attenuation of the light beams by said gases in said probe for providing a measure of the extend of absorption of each gas of interest in each of a plurality of separate channels, and a zero absorption channel providing a reference for the other channels, said electric circuit means providing an electric output representing each of said absorption measurements; and control means coupled to said transceiver including first means for converting said electric output to a corresponding percent modulation output for each of said gases of interest, for correcting each of said percent modulation outputs for temperature and pressure, for correcting said percent modulation output for interference between measured gases, and to provide corrected outputs representing the concentration of each of said measured gases, said control means providing an efficiency measurement value %CE=%CE Dry flue gas×%CE combustibles×1/100 where:

%CE Dry flue gas=$K_1[0.964+0.000135\%\ EA) - (0.000207+1.68\times10^{-6}\times\%EA)\ T_s]100$ $T_s$=flue gas exit/stack temperature °F. $K_1$=fuel sensitivity factor; oil=1.0, Natural gas=0.91

$$\%\ EA = \text{Excess air} = \left(\frac{20.9}{20.9 - \%\ O_{2D}} - 1\right) 100$$

% $O_{2D}$=% dry oxygen $$\%\ CE\ \text{Combustibles} = \left[1 - \frac{0.00028 \times CO}{100} K_2\right] 100$$

$K_2$=Ratio of total heat loss to all unburned combustibles to that only due to CO, ideally unity CO=ppm of carbon monoxide corrected to dry basis stoichiometric conditions.

* * * * *